Feb. 2, 1937. J. PERRY Plant Pat. 232
PEACH TREE
Filed Oct. 1, 1936
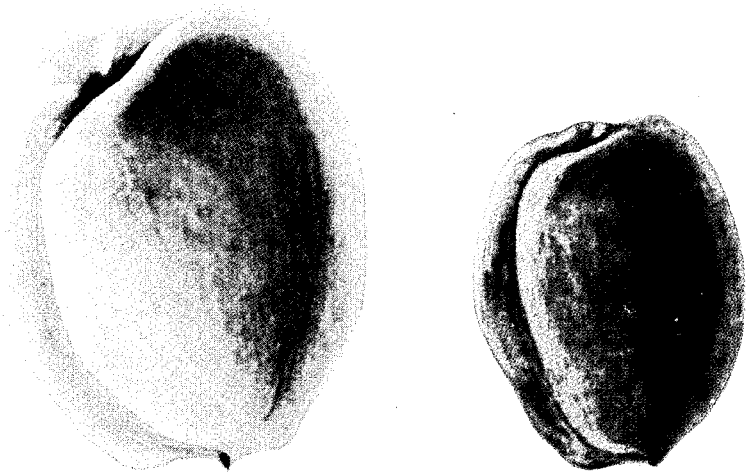
INVENTOR
Jay Perry
By Orville M. Kile
Plant Patent Agent Patented Feb. 2, 1937

Plant Pat. 232

UNITED STATES PATENT OFFICE

232

PEACH TREE

Jay Perry, Benton County, near Kennewick, Wash., assignor to Columbia & Okanogan Nursery Company, Wenatchee, Wash.

Application October 1, 1936, Serial No. 103,591

1 Claim. (Cl. 47—62)

My invention relates to a peach of the well known Elberta type and improvements relate particularly to color and date of maturity.

This variety is a sport of Elberta and was first discovered by me in 1928. As I was walking through my large orchard, I noticed an Elberta tree having one limb bearing red peaches. All other peaches on the tree and the surrounding trees were immature and without red coloring. By reproduction through budding, I had twenty-four trees bearing this same type of red peaches in 1932. I now have left sixteen of these original twenty-four trees and they have continued to produce peaches of the same kind each year, thus definitely establishing the new qualities of this variety.

With the exception of color and date of maturity, any standard description of an Elberta peach tree and fruit would also be a description of my new variety. A standard description of the Elberta peach, taken from "The Peaches of New York"—1917 edition, is as follows:

"Tree large, vigorous, upright-standing, dense-topped, hardy, very productive; trunk thick; branches stocky, smooth, reddish-brown intermingled with light ash-gray; branchlets with tendency to rebranch, with long internodes, olive-green, lightly overspread with dark red, glossy, smooth, glabrous with numerous conspicuous lenticels variable in size.

"Leaves six and three-fourths inches long one and three-fourths inches wide, oval to obovate-lanceolate; upper surface dull, dark olive-green, mottled and somewhat rugose; lower surface grayish-green; margin finely to coarsely serrate, often in two series, tipped with reddish-brown glands; petiole three-eighths inch long, with one to six reniform, greenish-yellow glands medium in size and variable in position.

"Flower buds large, pubescent, conical or obtuse, plump, appressed; flowers appear in mid-season; blossoms light pink near the center, darker pink toward the edges, one and one-fourth inches across; pedicles short, glabrous, green; calyx-tube reddish-green, orange-colored within, obconic, glabrous; calyx-lobes acute glabrous within, pubescent without; petals oval to ovate, bluntly notched near the base, tapering to broad, short claws red at the base; filaments one-half inch long, shorter than the petals; pistil pubescent at the ovary, longer than the stamens.

"Fruit matures in mid-season; two and three-fourths inches long and two and one-half inches wide; roundish-oblong or cordate, compressed, usually with a slight bulge at one side; cavity deep, abrupt to flaring, often mottled with red; suture shallow, deepening toward the apex; apex roundish, with a mamelon or pointed tip; color greenish-yellow changing to orange-yellow, from one-fourth to three-fourths overspread with red and with much mottling extending sometimes over nearly the entire surface; pubescence thick and coarse; skin thick, tough, separates from the pulp; flesh yellow, stained with red near the pit, juicy, stringy, firm but tender sweet or subacid, mild; good in quality; stone free, one and eleven-sixteenths inches long, one and one-sixteenth inches wide, broadly ovate, varying from flat to plump, sharp-pointed, decidedly bulged on one side, with pitted surfaces; ventral suture deeply furrowed along the sides, narrow, winged; dorsal suture deeply grooved, strongly winged."

The accompanying illustration shows a typical sample of the new peach and also an immature peach of the Elberta variety taken on the same date and under the same growing conditions.

As shown in the illustration, my new variety is much more highly colored with red than is the usual Elberta peach grown under similar soil and climatic conditions. This high red coloring develops on the peach even before maturity is reached.

This variety reaches a mature stage from ten days to two weeks earlier than the Elberta variety. This earlier maturity is of important commercial value because of the consequent lengthening of the shipping season for the well-established Elberta type of peach.

Thus having disclosed my invention, what I claim is:

A new and distinct variety of peach tree of the Elberta type, as herein described, characterized particularly by the high red coloring of its fruit as shown, and its earlier maturity.

JAY PERRY.